US005082730A

United States Patent [19]

Takeda et al.

[11] Patent Number: 5,082,730

[45] Date of Patent: Jan. 21, 1992

[54] STRETCHED POLYESTER FILM HAVING AN ANTISTATIC COATING COMPRISING A POLYMER HAVING PYRROLIDIUM RINGS IN THE MAIN CHAIN

[75] Inventors: Naohiro Takeda, Yokohama; Yuzo Otani, Tokyo; Nariaki Okajima, Yokohama; Masahiro Kita, Nagahama, all of Japan

[73] Assignee: Diafoil Company, Limited, Tokyo, Japan

[21] Appl. No.: 279,199

[22] Filed: Dec. 2, 1988

[30] Foreign Application Priority Data

| | | | |
|---|---|---|---|
| Dec. 4, 1987 | [JP] | Japan | 62-307272 |
| Dec. 22, 1987 | [JP] | Japan | 62-324469 |
| Dec. 28, 1987 | [JP] | Japan | 62-334957 |
| Dec. 28, 1987 | [JP] | Japan | 62-334958 |
| Dec. 28, 1987 | [JP] | Japan | 62-334959 |
| Dec. 28, 1987 | [JP] | Japan | 62-334961 |

[51] Int. Cl.[5] .......... B32B 7/00; C07D 295/00

[52] U.S. Cl. .......... 428/336; 428/480; 428/910; 428/922; 428/694; 430/528; 548/400; 260/DIG. 17

[58] Field of Search .......... 430/528; 428/480, 922, 428/336; 548/400; 260/DIG. 17

[56] References Cited

U.S. PATENT DOCUMENTS

| | | | |
|---|---|---|---|
| 3,607,286 | 9/1971 | Wood | 96/87 A |
| 3,976,661 | 8/1976 | Brooker et al. | 548/400 |
| 4,118,231 | 10/1978 | Mayama et al. | 430/528 |
| 4,196,001 | 4/1980 | Joseph et al. | 428/900 X |
| 4,214,035 | 7/1980 | Heberger | 428/340 |
| 4,294,739 | 10/1981 | Upson et al. | 430/528 X |
| 4,642,263 | 2/1987 | Culbertson | 428/336 |
| 4,810,624 | 3/1989 | Hardam et al. | 430/528 |

FOREIGN PATENT DOCUMENTS

| | | |
|---|---|---|
| 45-037032 | 11/1970 | Japan . |
| 59-216981 | 12/1984 | Japan . |

*Primary Examiner*—Merrell C. Cashion, Jr.
*Assistant Examiner*—Stevan A. Resan
*Attorney, Agent, or Firm*—Oblon, Spivak, McClelland, Maier & Neustadt

[57] ABSTRACT

Disclosed herein are a stretched antistatic laminate film comprising at least one coating layer containing a polymer having pyrrolidium rings in the main molecular chain, and a polyester film layer, a magnetic recording medium using the same, and a recording material for heat sensitive transfer printing using the same.

8 Claims, No Drawings

STRETCHED POLYESTER FILM HAVING AN ANTISTATIC COATING COMPRISING A POLYMER HAVING PYRROLIDIUM RINGS IN THE MAIN CHAIN

BACKGROUND OF THE INVENTION

The present invention relates a stretched antistatic laminate polyester film. More particularly, the present invention relates to a stretched antistatic laminate film prepared by coating a polymer having pyrrolidium rings to at least one surface of a polyester film and then stretching the resultant film, a magnetic recording medium having a magnetic layer on the stretched antistatic laminate film, a film having a silicon resin layer on the stretched antistatic laminate film, recording material for a thermal transfer printing having the stretched antistatic laminate film, as well as a method of manufacturing a film having the stretched antistatic laminate film.

Biaxially stretched polyester films have generally been used as a film having excellent properties but they have a fault of being easily charged.

As a method of preventing static charges, there are a method of kneading an anionic compound such as an organic sulfonate and organic phosphate, a method of vacuum-evaporating a metal compound, a method of coating an anionic compound, cationic compound or so-called electroconductive particles, etc. The method of kneading the anionic compound can be conducted at a reduced cost but it involves problems such as the limit for the antistatic effect, as well as deterioration in the adhesion between the film and the laminated layer due to blooming, lacking in water proofness and transferring the compound since the compound usable herein is a low molecular weight compound. The method of vacuum-evaporating the metal compound can provide excellent antistatic effect and the application use for transparent electroconductive films of the resultant films has been increased in recent years. However, since the production cost thereof is high, it is unfavorable to use the method for usual antistatic films although suitable to particular application uses. The method of coating the electroconductive carbon or electroconductive metal particles has relatively satisfactory antistatic effect and a merit capable of producing films at a relatively reduced cost, but it has a fault that the transparency of the films become worse.

In view of the above, a method of coating an anionic compound or cationic compound as the antistatic agent has generally been employed as the antistatic method of biaxially stretched polyester films.

For the method of manufacturing a biaxially stretched polyester film having a coating layer, there is known a coating and stretching method of applying a coating solution to a film, stretching the thus obtained film and subjecting to the thus stretched film heat-treatment (in-line coating method). As compared with the method of forming a coating layer by applying a coating solution to a biaxially stretched polyester film, since the film-formation and the coating can be practiced simultaneously in this method, wide film products can be obtained at a relatively reduced cost as well as the resultant films have good adhesion between the coating layer and the polyester film as the substrate, the thickness of the coating layer can be thinned and the surface property of the coating layer is excellent.

However, in the case producing an antistatic polyester film by the in-line coating method, since the antistatic agent is thermally instable, it results in volatilization or heat decomposition during stretching step and heat-treatment step, thereby sometime failing to obtain an expected antistatic effect in the case where the coating step and stretching step are practiced under usual conditions.

On the other hand, under the state where the conditions for the heat-treatment such as processing temperature or staying time of the film are moderated, although the volatilization or heat decomposition of the antistatic agent can be suppressed and as a result, an antistatic effect is exhibited, the resultant films have only insufficient mechanical strength, insufficient dimensional stability, etc.

There are some cases where such films can not always be applied, particularly, to magnetic recording material and recording material for heat sensitive transfer printing, or where a silicon resin lamination can not be carried out on such films.

As a result of the present inventors' earnest study for solving the foregoing problems, it has been found that a laminate film excellent in the antistatic effect and heat resistance can be manufactured easily with no particular attentions in the steps of coating, stretching and subjecting to heat-treatment in the in-line coating method, by using a coating solution containing a polymer having pyrrolidium rings in the main molecular chain as a coating solution which is to be coated at least on one surface of a polyester film, and the present invention has been accomplished based on such a finding.

SUMMARY OF THE INVENTION

In a first aspect of the present invention, there is provided a stretched antistatic laminate film comprising at least one coating layer containing a polymer having pyrrolidium rings in the main molecular chain, and a polyester film layer.

In a second aspect of the present invention, there is provided a magnetic recording medium comprising:

a stretched antistatic laminate film comprising at least one coating layer containing a polymer having pyrrolidium rings in the main molecular chain and a polyester film layer, and a magnetic layer laminated over the coating layer.

In a third aspect of the present invention, there is provided a recording material for a heat sensitive transfer printing comprising:

a stretched antistatic laminate film comprising at least one coating layer containing a polymer having pyrrolidium rings in the main molecular chain and a polyester film layer.

In a fourth aspect of the present invention, there is provided a method for producing a stretched antistatic laminate film, which comprises applying a coating solution containing a polymer having pyrrolidium rings in the main molecular chain to at least one surface of a polyester film, stretching the resultant laminate film and then subjecting the thus stretched film to heat-treatment.

DETAILED DESCRIPTION OF THE INVENTION

The polyester used in the present invention is a polyethylene terephthalate or polyethylene naphthalate in which not less than 80 mol % of the constituent is ethylene terephthalate or ethylene naphthalate respectively.

The polyester film in the present invention may contain, as occasion demands, inorganic particles, organic particles, organic lubricant, antistatic agent, stabilizer, dye, pigment and organic polymer as the ingredients of a composition. Fine particles are incorporated for providing a polyester film having slip property, in which the kind, size and blending amount of the protrusion forming agent is properly selected depending on the required properties such as slip property, transparency, etc. of products.

The molecular weight of the polymer having pyrrolidium rings in the main molecular chain in the present invention is from 500 to 1,000,000 and, preferably from 1000 to 500,000. If the molecular weight of the polymer is less than 500, although the antistatic effect can be obtained, the coating film of such a polymer has poor strength or becomes sticky tending to cause blocking. In a case where the molecular weight of the polymer exceeds 1,000,000 the viscosity of the coating solution is increased, tending to deteriorate the handlability or the coatability.

The polymer having pyrrolidium rings in the main molecular chain in the present invention is a polymer containing the repeating unit, for example, represented by the following formula (I) or (II):

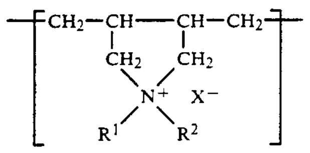

(I)

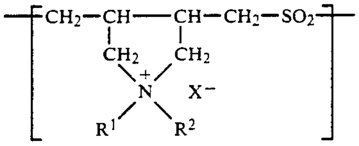

(II)

In the formula, $R^1$ and $R^2$ independently represent an alkyl group, alkyl group or phenyl group, in which the alkyl group or the phenyl group may be substituted with the groups described below.

As the substituent, for example, hydroxy group, amide group, carbo lower-alkoxy group, lower alkoxy group, phenoxy group, naphthoxy group, cyano group, thio lower-alkoxy group, thiophenoxy group, cycloalkyl group, tri-(lower-alkyl) ammonium lower-alkyl, nitro group which can substitute only on the alkyl group and the halogen group which can substitute only on the phenyl group may be exemplified.

Further, $R^1$ and $R^2$ may chemically bond to form a ring and, for example, $-CH_2)_m$ (m=integer of 2-5), $-CH(CH_3)-CH(CH_3)-$, $-CH=CH-CH=CH-$, $-CH=CH-CH=N-$, $-CH=CH-N=CH-$, $-CH_2)_2\ O-CH_2)_2$ and $-CH_2)_3\ O-(CH_2)_2-$ may be exemplified.

Only one of $R^1$ and $R^2$ may be a hydrogen atom.

In the formula, $X^-$ represents a halogen atom, for example $Cl^-$ and $Br^-$, an inorganic acid residue, for example, $\frac{1}{2}SO_4^{2-}$ and $\frac{1}{3}PO_4^{3-}$, an organic sulfonic acid residue, for example, $CH_3SO_4^-$ and $C_2H_5SO_4^-$, or a carboxylic acid residue, for example, $C_lH_{2l+1}COO^-$ (l=integer of 1 to 6).

The polymer of the formula (I) in the present invention is obtained by the cyclopolymerization of a compound represented by the formula (III):

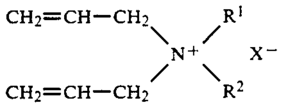

(III)

in the presence of a radical polymerization catalyst. Also, the polymer of the formula (II) is obtained by the cyclopolymerization of the compound of the formula (III) in a solvent, for example, sulfur dioxide.

The polymerization can be conducted by a known method in a solvent such as water or polar solvent, for example, methanol, ethanol, isopropanol, formamide, dimethylformamide, dioxane, acetronitrile and sulfur dioxide in the presence of a polymerization initiator such as hydrogen peroxide, benzoyl peroxide and tertiary butyl peroxide, but the solvent and polymerization initiator are not limited thereto.

As the polymer having pyrrolidium rings in the main molecular chain in the present invention, a copolymer of a compound having a carbon-carbon unsaturated bond and the compound of the formula (III), as a copolymerizable monomer, may be used.

By incorporating a crosslinking agent into the coating solution for the antistatic laminate film according to the present invention, the improvement of the strength of the coating layer as well as the improvement of blocking resistance, water proofness, solvent resistance, etc. can be attained. As crosslinking agents, those which are not electrostatically coagulative with a cationic polymer having the pyrrolidium rings in the main molecular chain, preferably water soluble or water dispersible, are preferred. The following crosslinking agents can be mentioned as follows but not limitatively.

(A) Methyloled or alkyloled compound

N-methyloled or N-alkyloled compound of melamine, urea, guanamine, acrylamide and polyamide compounds.

(B) Epoxy compound

Epoxy compound rendered hydrophilic by introducing hydroxy group or polyether group, or hydrophobic epoxy compound rendered water-dispersible by using surface active agent.

(C) Block polyisocyanate

Block polyisocyanates including those form low molecular weight to polyurethane types, in which the isocyanate groups are once blocked and inactivated by the reaction and then the so-called blocking agent is detached by heating to regenerate the isocyanate groups such that the polyisocyanate can be used also in the aqueous system.

(D) Aziridine compound

A compound having at least two aziridine groups.

(E) Coupling agent

A so-called coupling agent such as silicon compound containing metal element, titanium compound, aluminum compound, zirconium compound and zirco-aluminum compound.

(F) Others

Those compounds having groups reactive to heat, peroxide, light, etc., for example, vinylic or acrylic compounds, light sensitive resins, etc.

The amount of the crosslinking agent contained in the coating layer in the present invention is preferably from 3 to 50% by weight and, more preferably from 5 to 30% by weight. If the amount of the crosslinking agent is less than 3% by weight, no remarkable effect for improving the strength of the coating film can be obtained. On the other hand, if it exceeds 50% by weight, since the strength of the coating film is rather worsened or blocking resistance, etc. is deteriorated, it is not preferred.

For attaining more effective crosslinking effect, it may be preferred to blend a polymer having a group reactive with the crosslinking agent.

By incorporating a polyvinyl alcohol and a zirconium compound into the coating layer of the laminated film according to the present invention, a further improvement for the adhesion of the coating layer, the strength and the transparency of the coating film can be attained.

Polyvinyl alcohols in the present invention are saponification products of polyvinyl acetate or polyvinyl acetate copolymer, or modification products of polyvinyl alcohol. The saponification degree of the polyvinyl acetate or polyvinyl acetate copolymer is preferably from 50 to 100 mol %. The ratio of the copolymerizable monomer in the polyvinyl alcohol copolymer is preferably, from 0 to 50 mol %. As the copolymerizable monomer, those which are known, for example, in "Polyvinyl Alcohol", p 147-166, by C. A. Finch, published from John Wiley & Sons, 1973 or in Japanese Patent Application Laid-Open (KOKAI) 59-179648, etc., styrene, alkyl vinyl ether, vinyl versatate, (meth) acrylamide, olefin such as ethylene, propylene, α-hexene and α-octene, unsaturated acids such as (meth)acrylic acid, crotonic acid, maleic acid anhydride, fumaric acid and itaconic acid, as well as alkyl esters or alkali salts thereof, sulfonic acid-containing monomer such as 2-acrylamide-2-methylpropane sulfonic acid as well as alkali salt thereof, cationic monomer such as trimethyl-2-(1-(meth)acrylamide-1,1-dimethylethyl) ammonium chloride, 1-vinyl-2-methylimidazol and quarternarization product thereof, silyl-containing olefinically unsaturated monomer, etc. may be exemplified but it is not limited thereto. As the modification product of polyvinyl alcohol, those reaction products with acetalization product, reactive silane compound or reactive unsaturated monomer may be exemplified but it is not limited thereto.

The polymerization degree of the polyvinyl alcohols is preferably from 10 to 5,000, more preferably, from 30 to 3,000. As the polyvinyl alcohols, those usable in an aqueous solution or aqueous dispersion are preferred.

As the zirconium compound in the present invention, those showing cationic property such as zirconium nitrate and zirconium oxychloride as described in "Ink & Print", vol. 5, No. 1, pp 26–28, published 1987 may be exemplified but it is not limited thereto. It is considered that these compounds have a high molecular structure constructed by a so-called bridging structure with hydroxy groups as shown below.

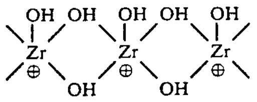

The coating layer comprising in the present invention from 30 to 92% by weight of the polymer having pyrrolidium rings in the main molecular chain from 5 to 97% by weight of polyvinyl alcohols and from 3 to 30% by weight of the zirconium compound is preferred. If the content of the zirconium compound is less than 3% by weight, no distinct effect for improving the transparency can not be obtained although depending on the content of the polyvinyl alcohol. On the other hand, if it is in excess of 30% by weight, the strength of the coating film or the stability of the coating solution may sometime be deteriorated.

The coating layer for the stretched antistatic laminate film comprising a polymer having pyrrolidium rings in the main molecular chain, a crosslinking agent, a polyvinyl alcohol and a zirconium compound can also be used in the present invention.

The coating solution in the present invention comprises the coating agents as described above specifically dissolved or dispersed in water. The medium for the coating solution is preferably water and an organic solvent such as alcohols, cellosolves, N-methyl pyrrolidone, etc. may be blended with the coating solution for the improvement of the coagulation stability of the coating agent, the coatability to the substrate polyester film, film forming property of the coating agent, etc.

In addition, for improving the block resistance or the slip property, the coating solution may contain, as fine inorganic particles such as silica, silica sol, alumina, alumina sol, zirconium sol, kaolinite, talc, calcium carbonate, titanium oxide, barium salt, carbon black, molybdenum sulfide, antimony oxide sol, etc. Further, if necessary, it may also contain defoaming agent, coatability improver, thickening agent, organic lubricant, organic polymeric particle, antioxidant, UV absorber, foaming agent, dye, etc. Furthermore, the coating solution according to the present invention may also contain those polymers other than the polymer as defined in the present invention, for improving the property of the coating solution or the coating layer.

As the method of applying the coating solution described above to a polyester film, one described in "Coating Method" by Yuji Hayazaki, published from Maki Shoten, 1979, such as (i) a method of applying a coating solution to a not-stretched polyester film by using a reverse roll coater, gravure coater, rod coater, air doctor or like other coating device, and sequential or simultaneous biaxially stretching, (ii) a method of coating a solution to a uniaxially stretched polyester film and further stretching in the direction perpendicular to the previous uniaxial stretching direction, and (iii) a method of coating a solution to a biaxially stretched polyester film and further, transversal and/or longitudinal stretching, (in-line coating method) may be exemplified.

The stretching step is carried out at a temperature from 60° to 130° C. and the stretching ratio expressed by the area ratio is at least 4 times, preferably from 6 to 20 times. The thus stretched film is subjected to heat-treatment at a temperature from 150° to 250° C. for 1 to 600 seconds.

Further, it is preferred to apply from 0.2 to 20% relaxation in the longitudinal and the transversal direction at a highest temperature zone of the heat-treatment and/or cleaning zone at the exit of the heat-treatment.

Particularly, it is preferred to use such a method of applying a coating solution to a uniaxially stretched polyester film which has been stretched by 2–6 times at a temperature from 60° to 130° C. by the roll stretching method, and with or without applying appropriate drying, stretching the resultant monoaxially stretched polyester film directly by 2–6 times a temperature from at 80° to 130° C. in the direction perpendicular to the previous stretching direction and then subjecting to heat-treatment at a temperature from 150° to 250° C. for 1 to 600 seconds.

According to this method, it is possible to dry the coating layer simultaneously with the stretching as well as the thickness of the coating layer can be reduced depending on the stretching ratio, by which a film suitable to the polyester film substrate can be manufactured at a relatively reduced cost.

The coating solution in the present invention may be coated only on one side or on both of the sides of the polyester film. In the case of coating only on one side thereof, it is possible to form a coating layer other than the coating solution in the present invention on the opposite side to provide the polyester film according to the present invention with other properties. For improving the coatability of the coating agent or the adhesion of the coating layer to the film, the film may be applied with chemical or electric discharge treatment before coating. Furthermore, electric discharging treatment may be applied to the coating layer after the formation thereof in order to improve the adhesion, coatability, etc. of the biaxially stretched polyester film according to the present invention to the coating layer.

The polyester film applied with the coating solution of the present invention obtained in the manner as described above has a thickness of the polyester film, preferably within a range from 3 to 500 μm and the thickness of the coating layer is preferably within a range from 0.01 to 5 μm and more preferably from 0.02 to 1 μm. If the thickness of the coating layer is less than 0.01 μm, no uniform coating layer can be obtained, tending to cause uneven coating in the product. On the other hand, if the thickness exceeds 5 μm, the slip property is deteriorated to become a difficulty in the film handling, which is not preferable.

The laminate film having the antistatic layer of the present invention is useful as a substrate for magnetic recording medium. That is, a magnetic recording medium excellent in antistatic effect can be obtained by laminating a magnetic layer over the antistatic layer (coating layer). The coating layer for the magnetic recording medium can include those containing a polymer having pyrrolidyl rings in the main molecular chain and, further, those containing a crosslinking agent and/or a polyvinyl alcohol and a zirconium compound in addition to the polymer having the pyrrolidyl rings in the main molecular chain.

The magnetic layer used in the present invention is a known so-called coating-type magnetic layer, in which magnetic powder such as iron oxide, pure iron, barium-ferrite type, etc. is dispersed together with a dispersant, abrasive agent, lubricant, antistatic agent, etc. into a binder such as of polyurethane, polyester, nitrocellulose, vinyl chloride - vinyl acetate copolymer or electron-ray curable binder. The thickness of the magnetic layer is preferably from 0.5 μm–15 μm and, more preferably from 1 μm to 10 μm. The magnetic layer may be disposed only on one side as a magnetic tape or on both sides as a floppy disc. Alternatively, it may be formed in a stripe-like manner to a portion of a substrate as a magnetic card.

Further, when a silicon resin layer is disposed on the antistatic layer (coating layer) of the laminate film according to the present invention, a laminate film useful for heat sensitive transfer printing, surface curing, mold releasing or slip-sheet can be obtained. The coating layer usable herein can include those containing a polymer having pyrrolidium rings in the main molecular chain and, further, those containing a polymer having pyrrolidium rings in the main molecular chain, as well as containing a cross-linking agent and/or a polyvinyl alcohol and a zirconium compound.

The silicone resin in the present invention has a polydimensional crosslinked structure of an organo polysiloxane obtained by the hydrolysis of an organo alkoxy silane and the self-condensation of a silanol. The structure or the degree of the cross-linking is different depending on the application uses. For example, crosslinking at high degree is not always necessary in view of the slip property and for the mold releasing use. However, it may be sometime necessary for increasing the crosslinking degree in the application use for the surface hardening for which scratch-resistance is demanded, or heat sensitive transfer application for which heat resistance is required. Accordingly, while there may be such a case of applying a solution or dispersion of a silicon resin without further increasing the crosslinking degree, heat-treatment is carried out after the coating to proceed so-called heat-curing in most of application uses.

According to the descriptions in "Functional Material", 1987, July, pp 30–39, the structural unit of the organo polysiloxane comprises the following four types:

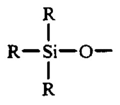
mono-functional

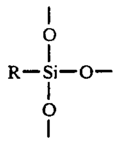
tri-functional

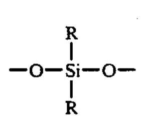
di-functional

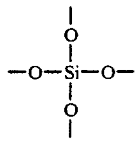
tetra-functional

While polysiloxanes of various skeltone structures can be obtained by the combination of them. Those having tri- or higher functionality are used for the improvement of the surface hardness and three-dimensional network polysiloxanes shown below can be obtained.

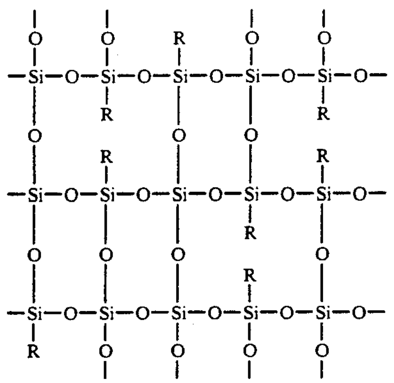

The polyorgano siloxane comprises the three types:

(1) All of substituents R are aliphatic acids or aromatic hydrocarbon residues.

(2) A portion of R is active to hydrolysis and condensation, such as -H, -Cl, -OH, -OR, etc. (silicon functional).

(3) A portion of R has organic functional group such as $—CH{=}CH_2$,

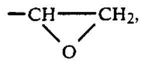

$—CH_2NH_2$, $—OOC—C(CH_3){=}CH_2$, $—CH_2Cl$, $—CH_2SH$ (carbon functional).

The carbon functional silane compound is known under the name of the silane coupling agent.

Among the silicon type paint, those paints mainly composed of methyl trimethoxysilane are particularly used frequently. For providing the hardened film with flexibility, a modification method of adding, for example, dimethyl dimethoxysilane is used and, on the other hand, tetra-functional, for example, tetramethoxy silane is added as the crosslinking agent in the case of intending to improve the hardness. Recently, there has been proposed a method of increasing the hardness by adding a colloidal silica to methyl trimethoxysilane.

The carbon functional silane has a specific property of both organic and inorganic bonds. Since the silicon functional silane has less organic bonds, it is poor in the adhesion with a plastic substrate and it is fragile although hard in view of the surface hardness. On the other hand, the carbon functional silane has excellent adhesion with the plastic substrate as can be seen in the example of using it as a primer for improving the adhesion, and the surface hardness is excellent homogenously for various evaluations. However, the carbon functional silane has such defect that it undergoes effects of light, water, heat, etc. thereby causing a problem in view of durability of the coating film and it is difficult to cause curing reaction as can be seen from the fact that higher temperature and longer time are required as compared with those in the curing reaction for the silicon functional silane.

Regarding the use of the silicon resin as the mold releasing agent, for example, to "Adhesion", vol. 28, No. 11, pp 484–489, published 1984, etc. may be referred.

Commercial products of the silicon resin are available from Dow Chemical Co., Ltd. Shinetsu Chemical Co., Ltd., Toshiba Silicone Co., Ltd., Toray Silicone Co., Ltd., Sumitomo Chemical Co., Ltd., Daisel Chemical Industries Ltd., Nippon Seika Co., Ltd., Daihachi Kagaku Kogyo Co., Ltd., etc. and they can be utilized as the silicone resin in the present invention but the silicon resin is not limited thereto.

The silicon resin layer may contain, as occasion demands, catalyst, crosslinking agent, fine organic or inorganic particles, coatability improver, colorant, stabilizer, lubricant, etc.

The silicone resin layer is usually laminated by the method according to the description in "Coating Method" by Yuji Harazaki, etc. described above, but it is not limited thereto.

The thickness of the silicon resin layer, although varying depending on the application use, is preferably not less than 0.05 μm and, more preferably from 0.05 to 5 μm in order to attain such effects.

Furthermore, the laminated film of the present invention can be used as a substitute for recording material (for example, paper) in a heat sensitive transfer recording and it is useful as recording material for use in heat sensitive transfer printing with excellent workability, with no attraction and deposition of dusts and improved transfer property, when it is used as the projection material for use in overhead projectors, second master for drawing use, etc.

The present invention is explained in more detail in the following Examples; however, it should be recognized that the scope of the present invention is not restricted to these Examples.

The evaluation in the examples are according to the following methods.

(1) Antistatic property

A: Charge attenuation

Using a Static Honestmeter (trade name, Shisido Shokai Co., Ltd.), a 10 kV of voltage was applied to a discharge electrode positioned at 2 cm height over a specimen under the atmosphere of 23° C. and 50% RH to charge static charges to a film and the electric discharge was interrupted after the saturation of the amount of satatic charges. Then, the charge attenuation of the specimen was measured by a potentiometer situated at a position 2 cm higher above the specimen and half-decay time was judged.

less than 5 sec: extremely satisfactory
5–30 sec: satisfactory
30–600 sec: somewhat satisfactory
more than 600 sec: failed B: Inherent surface resistivity To a coaxial type electrode, Model 16008A (trade name, Yokogawa-Hewlett Packard Ltd.), having an inner electrode of 50 mm diameter and an outer electrode of 70 mm diameter, a specimen was set under the atmosphere of 23° C. and 50% RH, 100 V of voltage was applied and the inherent surface resistivity of the specimen was measured by using a high resistmeter 4329A (trade name, Yokogawa Hewlett Packard Ltd.).

C: Ash test

The surface of a specimen was rubbed by 10 reciprocal strokes with gauze held at a tip of a finger under the atmosphere of 23° C. an 50% RH to charge static charges a film. Then, the specimen was brought closer to Saylloid 150 which is fine silica particles (trade name, Fuji Davison Co., Ltd.) and the distance at which the fine particles were adsorbed to the film was measured and judged by the following standards:

0–0.5 cm: satisfactory 0.5–2 cm: somewhat satisfactory more than 2 cm: failed

When the coating film is damaged by rubbing with the gauze, the antistatic effect is also eliminated and accordingly, the present test also provides an evaluation for the strength of the coating film.

(2) Friction coefficient

Test was conducted by the method improved that measurement can be made for a tape-like sample in accordance with ASTM D-1894. A film with no coating layer and a film applied with a coating layer were superposed to each other so that the coating layer is on the inside, and the obtained superposed film was cut into a tape-like form of 15 mm width. Measurement was made under a load of 100 g and at a tensile rate of 20 mm/min. The measurement was conducted under the atmosphere of 23° C. and 50% RH.

(3) Transparency

According to JIS K 6714, haze was measured by using an integration type turbidimeter NDH-20D (trade name, Nippon Denshoku Kogyo Co., Ltd.).

(4) Surface roughness

According to JIS B0601, the center line average roughness Ra was measured as below.

The surface of a film was measured over 25 mm using a Surfcorder SE-3F (trade name, Kosaka Kenkyusho Co., Ltd.) which is a contact type surface roughness meter using PUDJ of 2.0 μm diameter as a probe and under the condition of 30 mg of load and at a rate of 0.1 mm/sec. A coarse curve was determined by magnifying the direction of the standard length by 100 times and the direction of the surface roughness by 50,000 times. A portion for the measured length L is sampled the direction of the center line from the coarse curve. When expressing the coarse curve as y=f(x) while taking the center line for the sampled portion on X-axis and the direction in the longitudinal factor on Y-axis, the value given by the following equation is expressed by the unit of μm:

$$Ra = \frac{1}{L} \int_{0}^{L} |f(x)|\,dx$$

Upon measurement, the cut-off value is 0.08 mm. Measurement was made for 12 points and the average value was determined with respect to 10 points excluding the maximum value and the minimum value.

(5) Blocking resistance

The surface with a coating layer and the surface with no coating layer, or each of the surfaces with a coating layer of polyester films were superposed respectively under the atmosphere of 40° C. and 80% RH for one hour in a thermo hygrostat, applied with a load of 10 kg/cm$^2$ by a press and then treated in the thermo hygrostat for 20 hours. Then, such a treated film of 20 cm width was measured according to the method of ASTM D-1893 by separating them using a piano wire.

(6) Strength of the coating film

Using HEIDON-14 (trade name, Shinto Kagaku Co., Ltd.), which is a surface property tester and measurement was made by applying a load on a sapphire probe of 0.25 mm diameter and at a scratching rate of 100 mm/mm. The load at which the coating layer was peeled off from the substrate polyester film was judged based on the photograph for the surface of the film after the scratch test by using a microscope.

(7) Solvent resistance

A pencot F-1 (trade name, Asahi Chemical Industry Co., Ltd.), which is dustless cotton impregnated with 0.4 ml of a solvent was placed over a specimen film on a glass plate and, further thereover, a cylindrical weight with 23 mm diameter and 100 g of weight was placed. One end of the dustless cotton was connected to a pulling machine and displaced at a rate of 60 mm/sec. The judgement for the solvent resistance was conducted by the presence or absence of scratches caused by the fibers of dustless cotton. The solvent used herein was tetrahydrofuran, methyl ethyl ketone, cyclohexanone, toluene and n-heptane.

(8) Heat sensitive transfer property

A: Monochromatic image

As a heat sensitive transfer apparatus, TLP 240B-GN (Gotenba Manufacturing Co., Ltd.) was used. Heat sensitive transfer material having black ink layer (Fuji Kagakushi Co., Ltd.) was used. The conditions for the heat sensitive transfer was electric turning-on time of 4 mm/sec, electric turning-on energy of 2 mm joule per 1 dot and line width of transfer ink of 0.1 mm. As the standard for the judgement of the transfer property of the heat sensitive transfer ink, those cases where not less than 90% of the ink layers heat-transferred linearly were transferred onto the polyester film were judged satisfactory, whereas the results less than 90% were judged unsatisfactory.

B: Color image

Color scanner printer CX-5000 (trade name, Sharp Corporation) was used as the heat sensitive transfer apparatus. As the heat sensitive transfer material, those comprising four colors, that is, yellow, cyan, magenta and black, manufactured by Ikekawa Kappansho Co., Ltd. were used. As the conditions for the apparatus, the printing density was made low so as to easily recognize the difference by using a printing density control knob attached to apparatus. For the Judgement of the image gradation, a color chart No. 22 from Image Electronics Association was utilized.

Example 1

Polyethylene terephthalate having an intrinsic viscosity of 0.65 was melt-extruded at a temperature from 280°–300° C. and cast on a cooling drum while using an electrostatic cooling method thereby obtaining an amorphous film of 820 μm in thickness.

A coating solution of a Sharoll DC-902P (trade name, Daiichi Kogyo Seiyaku Co., Ltd.) which is a polymer comprising a constitution unit represented by the formula (I) was coated on one surface of a polyester film after longitudinally stretching the thus obtained amorphous polyester film by 3.3 times at 90° C. but before transversally stretching. Then, the coated film was stretched transversally by 3.3 times at 110° C. and then subjected to heat-treatment at 210° C. to obtain polyester films having coating layers of various coating thickness (thickness of the polyester film: 75 μm). The relation between the thickness of the coating layer of the film and the antistatic property was as described below.

TABLE 1

| Coating layer thickness (μm) | 0.015 | 0.030 | 0.045 | 0.100 |
|---|---|---|---|---|
| Charge attenuation | somewhat satisfactory | satis-factory | extremely satisfac-tory | extremely satisfac-tory |
| Inherent surface resistivity | somewhat satisfactory | satis-factory | extremely satisfac-tory | extremely satisfac-tory |

That is, the polyester films according to the present invention were useful as the antistatic film.

Example 2

PAS-88 (trade name, Nitto Boseki Co., Ltd.) which is a polymer comprising the structural unit represented by the formula (II) was coated in the same manner as in Example 1 to obtain a film having the coating layer of 0.045 μm in thickness and the substrate polyester film of 75 μm in thickness.

The charge attenuation and the inherent surface resistivity of this film were extremely satisfactory.

That is, the polyester film of the present invention was useful as the antistatic film.

Example 3

A coating solution (A) containing 70 parts by weight (solid content) of Sharoll DC-902P (trade name) used in Example 1 and 30 parts by weight (solid content) of polyvinyl alcohol having a saponification degree of 88% and polymerization degree of 800 as well as a coating solution (B) containing 35 parts by weight (solid content) of Sharoll DC-902P and 65 parts of the polyvinyl alcohol described above were respectively coated in the same procedures as in Example 1 to obtain films having each coating layer of 0.045 μm in thickness and substrate polyester film of 75 μm in thickness.

The charge attenuation and the inherent surface resistivity of the films in this example were extremely satisfactory for the film using the coating solution (A) and satisfactory for the film using the coating solution (B), respectively.

That is, the polyester films according to the present invention were useful as the antistatic film.

Example 4

Polyethylene terephthalate having an intrinsic viscosity of 0.65 and containing titanium oxide as additive particles was melt-extruded at a temperature of 280°-300° C. and then cast on a cooling drum while using the electrostatic cooling method to obtain an amorphous film of 405 μm in thickness. The thus obtained amorphous film was stretched longitudinally by 3.5 times at 95° C. and then a coating solution containing 55 parts by weight (solid content) of Sharoll DC-303P (trade name, Daiichi Kogyo Seiyaku Co., Ltd.) which is a polymer represented by the formula (I) and 45 parts by weight (solid content) of polyvinyl alcohol used in Example 3 was coated on both surface of the resultant film and, further, the film was stretched transversally by 3.5 times, and subjected to heat-treatment at 210° C. to obtain a film having a coating layer of 0.045 μm in thickness and the substrate polyester film of 33 μm in thickness.

The charge attenuation and the inherent surface resistivity of the film in this example were extremely satisfactory.

That is, the polyester film of this example was useful as the antistatic film.

Comparative Example 1

Polyethylene terephthalate having an intrinsic viscosity of 0.65 was melt-extruded at a temperature from 280° C.-300° C. and cast on a cooling drum while using the electrostatic cooling method to obtain an amorphous film of 820 μm in thickness. The thus obtained amorphous film was longitudinally stretched by 3.3 times at 95° C. and then transversally stretched by 3.3 times at 110° C. and then subjected to heat-treatment at 210° C. to obtain a biaxially stretched polyester film of 75 μm in thickness.

The charge attenuation of the film was unsatisfactory and the result of the force-moistening method was also unsatisfactory. The inherent surface resistivity of the resultant film was poor such as $10^{15}$–$10^{16}$ □/Ω.

Examples 5-10

In the same procedures as in Example 1, the following coating solutions (C)-(H) were applied to obtain biaxially stretched polyester films having each coating layer of 0.05 μm in thickness and the substrate film of 75 μm in thickness.

These films were satisfactory for the inherent surface resistivity and there were obtained improving effect for the strength of the coating film and the blocking resistance. The results obtained are shown in Table 2 and Table 3.

(C) A coating solution containing 40 parts by weight (solid content) of Sharoll DC-303P (trade name), which is a polymer having pyrrolidium rings in the main molecular chain, 50 parts by weight (solid content) of Gosenol GL05 (trade name, Nippon Gosei Kagaku Kogyo Co., Ltd.),which is polyvinyl alcohol and 10 parts by weight (solid content) of alkylolmelamine as a crosslinking agent.

(D) A coating solution containing 40 parts by weight (solid content) of DC-303P (trade, name), 50 parts by weight, (solid content) of GL05 (trade name) and 10 parts by weight (solid content) of crosslinking agent zircozol AC-2 (trade name, Daiichi Kigenso Kagaku Kogyo Co., Ltd.).

(E) A coating solution containing 40 parts by weight (solid content of DC-303P (trade name), 40 parts by weight (solid content) of GL05 (trade name), 10 parts by weight (solid content) of Denacol EX-5121 (trade name, Nagase Kasei Co., Ltd.), which is a aqueous epoxy compound crosslinking agent, and 10 parts by weight (solid content) of ZC-2 (trade name).

(F) A coating solution containing 40 parts by weight (solid content) of DC-303P (trade name), 40 parts by weight (solid content) of GL05 (trade name), 10 parts by weight (solid content) of ZC-2 (trade name) and 10 parts by weight (solid content) of alkylolamine.

(G) A coating solution containing 30 parts by weight (solid content) of DC-902P (trade name, Daiichi Kogyo Seiyaku Co., Ltd.), which is a polymer having pyrrolidium rings in the main molecular chain, 40 parts by weight (solid content) of PVA R-1130 (trade name, Kurare Co., Ltd.), which is polyvinyl alcohol having silicon group and 10 parts by weight (solid content) of ZC-2 (trade name).

(H) A coating solution containing 40 parts by weight (solid content) of PAS-88 (trade name, Nitto Boseki Co., Ltd.), which is the polymer having pyrrolidium rings and sulfone groups in the main molecular chain, 40 parts by weight (solid content) of GL05 (trade name), 10 parts by weight (solid content) of ZC-2 (trade name) and 10 parts by weight (solid content) of alkylolmelamine.

TABLE 2

| | Coating solution | Inherent surface resistivity (Ω/□) | Strength of coating film (g) | Friction test $\mu_a$ | Friction test $\mu_d$ |
|---|---|---|---|---|---|
| Comparative Example 1 | None | not less than $10^{15}$ | — | 0.79 | 0.83 |
| Example 5 | C | $7 \times 10^9$ | 5 | 0.69 | 0.90 |
| Example 6 | D | $8 \times 10^9$ | 5 | 0.70 | 0.77 |
| Example 7 | E | $9 \times 10^9$ | 50 | 0.50 | 0.58 |

TABLE 3

| | Coating solution | Haze (%) | Inherent surface resistivity (Ω/□) | Blocking resistance (g) |
|---|---|---|---|---|
| Comparative Example 1 | None | 1.8 | Not less than $10^{15}$ | 3 |
| Example 8 | F | 1.8 | $9 \times 10^9$ | 94 |
| Example 9 | G | 2.1 | $1 \times 10^9$ | 90 |
| Example 10 | H | 1.9 | $3 \times 10^9$ | 120 |

Comparative Example 2

A magnetic layer was disposed on a film obtained in Comparative Example 1 (surface roughness Ra=0.006 μm) in the following manner.

The magnetic paint was prepared by dispersing a paint of the following composition in a vibration mill for 24 hours, blending 5.6 parts by weight (solid content) of Coronate L (trade name, Nippon Polyurethane Co., Ltd.), which is polyisocyanate and then mixing them for 20 min. Paint Composition (1) 65 parts by weight (solid content) of Nipporan N-5033 (trade name, Nippon Polyurethane Co., Ltd.), which is polyurethane.

(2) 20 parts by weight (solid content) of OHLESS FM200 (trade name, Daisel Kagaku Kogyo Co., Ltd.), which is nitrocellulose.

(3) 30 parts by weight (solid content) of 10000 GKT (trade name, Denki Kagaku Kogyo Co., Ltd.), which is vinyl chloride - vinyl acetate copolymer.

(4) 12 parts by weight (solid content) of carbon black #30 (trade name, Mitsubishi Kasei Kogyo Co., Ltd.), which is carbon black.

(5) 4 parts by weight (solid content) of soybean lecithin (Kishida Kagaku Co., Ltd.)

(6) 371 parts by weight (solid content) of γ-LOP (trade name, Titan Kogyo Co., Ltd.), in which γ-iron oxide.

(7) 900 parts by weight of equi-weight mixture of toluene, methyl ethyl ketone and methyl isobutyl ketone as a solvent.

The magnetic paint described above was coated and dried at 80° C. for 1 min and subjected to aging treatment at 80° C. for 20 hours to form a magnetic layer of 5 μm in thickness.

Example 11

After coating the following coating solution (I) on both sides of the film in Comparative Example 1 after longitudinally stretching but before transversally stretching, the film was fabricated in the same manner as in Comparative Example 1 to obtain a biaxially stretched polyester film having the coating layer of 0.04 μm in thickness and the substrate film of 75 μm in thickness. A magnetic layer was coated over the coating layer of the resultant film to obtain a magnetic recording medium.

(I) A coating solution containing 45 parts by weight (solid content) of Sharoll DC-303P (trade name, Daiichi Kogyo Seiyaku Co., Ltd.), which is a polymer having pyrrolidium rings on the main molecular chain, 35 parts by weight (solid content) of Gosenol GL05 (trade name, Nippon Gosei Kagaku Kogyo Co., Ltd.) which is polyvinyl alcohol, 10 parts by weight (solid content) of Zircozol ZC-2 (trade name, Daiichi Kigenso Kagaku Kogyo Co., Ltd.), which is a zirconium compound and 10 parts by weight (solid content) of alkylolmelamine.

Example 12

Polyethylene terephthalate having an intrinsic viscosity of 0.64 and containing titanium oxide as additive particles was melt-extruded and cast on a cooling drum while using the electrostatic cooling method to obtain an amorphous sheet of 415 μm in thickness. The sheet was longitudinally stretched by 3.3 times at 90° C., an aqueous dispersion coating solution (J) having the same blending composition as that in Example 11 except for using 10 parts by weight (solid content) of Denacol EX-521 (trade name, Nagase Kasei Co., Ltd.) which is an aqueous epoxy compound, instead of alkylolmelamine as the ingredient of the coating solution of Example 11 was coated on both surfaces of the resultant film, and the thus coated film was further stretched transversally at 110° C. and then subjected to heat-treatment at 215° C. to obtain a biaxially stretched polyester film having the coating layer of 0.06 μm in thickness and the substrate film of 38 μm in thickness.

The surface roughness of the resultant film was Ra=0.005 μm. A magnetic layer was coated on the coating layer of the film to obtain a magnetic recording medium.

The properties of the film and the magnetic recording media thus obtained are collectively shown in Table 4.

TABLE 4

| | Properties of antistatic layer | | | | | Properties of magnetic recording medium | |
|---|---|---|---|---|---|---|---|
| | Solvent resistance | | | Inherent surface resistivity (Ω/□) | Charge attenuation (sec) | Inherent surface resistivity (Ω/□) | Charge attenuation (sec) |
| | Toluene | MEK(1) | MIBK(2) | | | | |
| Comparative Example 2 | — | — | — | not less than $10^{15}$ | No attenuation | $2 \times 10^{12}$ | 60 |
| Example 11 | * | * | * | $4 \times 10^8$ | not charge | $1 \times 10^{10}$ | 10 |

TABLE 4-continued

| | Properties of antistatic layer | | | | | Properties of magnetic recording medium | |
|---|---|---|---|---|---|---|---|
| | Solvent resistance | | | Inherent surface | Charge attenuation | Inherent surface | Charge attenuation |
| | Toluene | MEK(1) | MIBK(2) | resistivity (Ω/□) | (sec) | resistivity (Ω/□) | (sec) |
| Example 12 | * | * | * | $6 \times 10^8$ | not charge | $2 \times 10^{10}$ | 10 |

*Satisfactory
(1)MEK: methyl ethyl ketone
(2)MIBK: methyl isobutyl ketone

Example 13

Polyethylene terephthalate having an intrinsic viscosity of 0.65 was melt-extruded and cast on a cooling drum while using the electrostatic cooling method to obtain an amorphous sheet of 415 μm in thickness. The sheet was longitudinally stretched by 3.3 times at 95° C., the coating solution (I) used in Example 11 was coated on one surface of the resultant film, and the thus obtained film was further stretched transversally by 3.3 times at 110° C. and subjected to heat-treatment at 210° C. to obtain a biaxially stretched polyester film having the coating layer of 0.04 μm in thickness and the substrate film of 38 μm in thickness. The silicone resin coating solution (K) was coated over the coating layer of the resultant film, dried and then subjected to heat-treatment to obtain a laminated film having the silicone resin layer of 0.06 μm in thickness.

Example 14

In the same procedures as in Example 13 except for using the coating solution (J) used in Example 12 instead of the coating solution (I) in Example 13, to obtain a laminated film.

Example 15

In the same procedures as in Example 13 except for using a silicon resin coating solution (L) instead of the silicon resin coating solution (K) in Example 13, to obtain a laminated film.

Example 16

In the same procedures as in Example 14 except for using the silicon resin coating solution (L) instead of the silicon resin coating solution (K) in Example 14, to obtain a laminated film.

The laminated films obtained in Examples 13–16 were excellent as a retainer for magnetic cassette tapes.

Example 17

Polyethylene terephthalate having an intrinsic viscosity of 0.66 was melt-extruded in the same procedures as in Example 13 to obtain an amorphous sheet of 272 μm in thickness. Further, after longitudinally stretching in the same manner as in Example 13, the coating solution (I) in Example 13 was coated on one surface and applied with the same procedures as in Example 13 to obtain a biaxially stretched polyester film having the coating layer of 0.04 μm in thickness and the substrate film of 25 μm in thickness. A silicon resin coating solution (M) was coated over a coating layer of the resultant film, dried and then subjected to heat-treatment to obtain a laminated film having the silicon resin layer of 0.15 μm in thickness. The resultant laminated film had satisfactory properties as the releasing film.

Example 18

After coating and drying a silicon resin coating solution (N) instead of the silicon resin solution (M) in Example 17, the resultant film was subjected to heat-treatment to obtain a laminated film having the silicon resin layer of 2 μm in thickness. When the coating layer surface of the resultant laminated film was rubbed with steel wires of #000 (item No.) no scratches were formed and the film was excellent in the surface hardenability and suitable as an inner linear film for automobile window glass.

Example 19

Polyethylene terephthalate film having an intrinsic viscosity of 0.66 was melt-extruded to obtain an amorphous film of 55 μm in thickness. The film was longitudinally stretched by 3.5 times at 85° C., applied with a coating solution (J), stretched transversally by 3.3 times at 110° C. and longitudinally by 1.1 times at 120° C., and then subjected to heat-treatment at 215° C. to obtain a biaxially stretched polyester film having the coating layer of 0.05 μm in thickness and the substrate film of 4.0 μm in thickness. A coating solution (O) was coated and dried over the coating layer of the resultant film, and subjected to heat-treatment to obtain a laminated film having the silicon resin layer of 0.2 μm in thickness. The resultant laminated film showed satisfactory handlability and, when a melt-wax type ink was formed to the rear face of the silicon resin layer and used as a toner film for heat sensitive transfer process, so-called twining caused by the charge of the film was not observed, passage relative to the thermal head and printability were satisfactory and the product could be served for practical use as heat sensitive transfer film.

Comparative Examples 3 and 4

Biaxially stretched polyester films were obtained by the procedures in Example 11 without applying the coating solution. Then, the laminated film disposed with the silicon resin layer by the coating solution (K) was referred as Comparative Example 3 and disposed with the silicon resin layer using the coating solution (L) was referred to as the Comparative Example 4.

Properties of the resultant films are collectively shown in Table 5. Also the compositions of the silicon resin coating solution are shown below.

Composition for Coating solution (K)

A solution prepared by diluting a blend of KS778 (trade name, Shinetsu Chemical Co., Ltd.) which is an addition reaction type silicon resin and PL-7 (Shinetsu Chemical Co., Ltd.) which is a platinum catalyst with a solvent mixture of toluene, methyl ethyl ketone and n-heptane.

Composition for Coating solution (L)

A solution prepared by diluting a blend of X-62-2113 (trade name, Shinetsu Chemical Co., Ltd.) which is an addition reaction type silicon resin and PL-8 (Shinetsu Chemical Co., Ltd.), which is a platinum catalyst with a solvent mixture of toluene, methyl ethyl ketone and n-heptane.

Composition for Coating solution (M)

A solution prepared by diluting a blend of silicon varnish FSXF-2560 (trade name, Dow Coning Co., Ltd.) which is a dehydrogenating condensation type silicon resin and K-1638 (Dow Chemical Co., Ltd.), which is a platinum catalyst with a solvent mixture of toluene, methyl ethyl ketone and n-heptane.

Composition for coating solution (N)

Blend of X-12-922 (trade name, Shinetsu Chemical Co., Ltd.) containing methyl trimethoxysilane as the main component and also containing colloidal silica, and acetic acid as a catalyst.

Composition for coating solution (O)

A solution prepared by diluting a blend of Si coat 727 (trade name, Daihachi Kagaku Kogyo Co., Ltd.) comprising hydrolysis product of an alkoxy silane mainly composed of methyl trimethoxysilane and a melamine resin KF-352 (trade name, Shinetsu Chemical Co., Ltd.), which is polyether-modified silicon oil, and Eposta-S (trade name, Nippon Shokubai Kagaku Co., Ltd.), which is fine particles of benzoguanamine resin, with a mixed solvent of toluene, methyl ethyl ketone, n-heptane, cellosolve and methanol.

TABLE 5

| | Properties of antistatic layer | | | Properties of laminate |
|---|---|---|---|---|
| | Solvent resistance | Inherent surface resistivity (Ω/□) | Charge attenuation (sec) | Charge attenuation (sec) |
| Comparative Example 3 | — | not less than $10^{15}$ | no attenuation | no attenuation |
| Comparative Example 4 | — | not less than $10^{15}$ | no attenuation | no attenuation |
| Example 13 | Satisfactory | $4 \times 10^8$ | not charge | 1 |
| Example 14 | Satisfactory | $6 \times 10^8$ | not charge | 1 |
| Example 15 | Satisfactory | $4 \times 10^8$ | not charge | 1 |
| Example 16 | Satisfactory | $6 \times 10^8$ | not charge | 1 |
| Example 17 | Satisfactory | $4 \times 10^8$ | not charge | 5 |
| Example 18 | Satisfactory | $4 \times 10^8$ | not charge | 22 |
| Example 19 | Satisfactory | $6 \times 10^8$ | not charge | 8 |

Example 20

Polyethylene terephthalate having an intrinsic viscosity of 0.65 was melt-extruded at 280°-300° C. and cast on a cooling drum while using the electrostatic cooling method to obtain an amorphous film of 550 μm in thickness. The film was longitudinally stretched by 3.3 times at 95° C. Then, an aqueous dispersion containing 40 parts by weight (solid content) of Sharoll DC-303P (trade name, Daiichi Kogyo Seiyaku Co., Ltd.), which is a polymer having pyrrolidium rings on the main molecular chain, 35 parts by weight (solid content) of Gosenol GL05 (trade name, Nippon Gosei Kagaku Kogyo Co., Ltd.), which is polyvinyl alcohol, 10 parts by weight (solid content) of Zircozol ZC-2 (trade name, Daiichi Kigenso Kagaku Kogyo Co., Ltd.) which is a zirconium compound, 5 parts by weight (solid content) of alkylolmelamine and 10 parts by weight (solid content) of Denacol EX-521 (trade name, Nagase Kasei Co., Ltd.) which is an aqueous epoxy compound was coated on both surfaces of the film. Then, the film was stretched transversally by 3.3 times at 110° C. and subjected to heat-treatment at 210° C. to obtain a biaxially stretched polyester film having the coating layer of 0.06 μm in thickness and the substrate film of 50 μm in thickness.

The resultant film had a haze of 3.0, stationary friction coefficient of 0.42, dynamic friction coefficient of 0.49 and inherent surface resistivity of $4 \times 10^9$ Ω/□. The results of the test for the charge attenuation and ash test of the film were satisfactory and the heat sensitivity transfer property of the film was also satisfactory. When the film was released from a rolled state and tested in a heat sensitive transfer apparatus of applying heat sensitive transfer and cutting into A-4 print size, the passing property, heat sensitive transfer property, cutting workability, arranging and stripping property of stacked films of A4-size printed products were satisfactory.

That is, the film can be served to practical use as the recording material for heat sensitive transfer printing.

What is claimed is:

1. A stretched antistatic laminate film comprising at least one coating layer having a thickness in the range from 0.01 to 5 μm and containing a polymer having pyrrolidium rings in the main chain of the polymer on a polyester film layer, said polymer having pyrrolidium rings in the main chain of the polymer containing the repeating unit represented by the following formula (I) or (II):

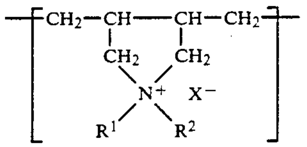

(I)

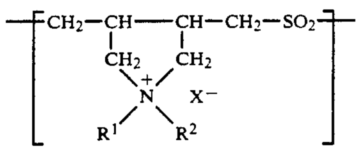

(II)

wherein $R^1$ and $R^2$ independently represent respectively an alkyl or phenyl group which may be substituted, $R^1$ and $R^2$ may chemically bond to form a ring, or one of $R^1$ and $R^2$ represents a hydrogen atom and $X^-$ represents a halogen atom, an inorganic acid residue, and organic sulfonic acid residue or a carboxylic acid residue, said coating layer being formed on the polyester film layer by an in-line coating method, said in-line coating method comprising applying said coating layer to a uniaxially stretched polyester film which has been uniaxially stretched by 2-6 times at a temperature from 60 to 130° C. by a roll stretching method and then optionally drying, stretching the resultant coated uniaxially stretched polyester film by 2-6 times at a temperature from 80° to 130° C. in the direction perpendicular to the uniaxial stretching direction and then heat treating the coated stretched polyester film at a temperature from 150° to 250° C. for 1 to 600 seconds.

2. A stretched antistatic laminate film according to claim 1, wherein the coating layer further contains a polyvinyl alcohol and a zirconium compound.

3. A stretched antistatic laminate film according to claim 1, wherein the coating layer further contains a crosslinking agent.

4. A stretched antistatic laminate film according to claim 1, wherein the coating layer further contains a polyvinyl alcohol, cationic zirconium compound and a crosslinking agent.

5. A stretched antistatic laminate film according to any one of claims 1 to 4, wherein a silicon resin layer comprising an organopolysiloxane is further laminated over the coating layer.

6. A stretched antistatic laminate film according to claim 1, wherein the molecular weight of the polymer having pyrrclidium rings in the main molecular chain is from 500 to 1,000,000.

7. The stretched antistatic laminate film of claim 1, wherein said coating layer has a thickness in the range from 0.02 to 1 μm.

8. The stretched antistatic laminate film of claim 1, wherein said laminate film has a thickness in the range from 3-500 μm.

* * * * *